United States Patent [19]
Ide et al.

[11] Patent Number: 5,455,375
[45] Date of Patent: Oct. 3, 1995

[54] PROCESS FOR PREPARING ADIPIC ACID

[75] Inventors: Tohru Ide; Masahisa Yokota, both of Nobeoka, Japan

[73] Assignee: Asahi Kasei Kogyo Kabushiki Kaisha, Osaka, Japan

[21] Appl. No.: 190,195

[22] PCT Filed: Apr. 9, 1993

[86] PCT No.: PCT/JP93/00457

§ 371 Date: Jul. 25, 1994

§ 102(e) Date: Jul. 25, 1994

[87] PCT Pub. No.: WO94/24083

PCT Pub. Date: Oct. 27, 1994

[51] Int. Cl.$^6$ ............ C07C 55/00; C07C 55/14; C07C 51/31
[52] U.S. Cl. ............ 562/590; 562/512.4; 562/523
[58] Field of Search ............ 562/590, 512.4, 562/523

[56] References Cited

U.S. PATENT DOCUMENTS

| | | | |
|---|---|---|---|
| 3,726,917 | 4/1973 | Brunie et al. | 562/590 |
| 4,254,283 | 3/1981 | Mock | 562/530 |
| 4,605,790 | 8/1986 | Wojtkowski | 568/750 |
| 4,814,511 | 3/1989 | Neubauer et al. | 568/342 |
| 5,321,157 | 6/1994 | Kollar | 562/543 |

FOREIGN PATENT DOCUMENTS

| | | |
|---|---|---|
| 31-421 | 1/1956 | Japan. |
| 37-6506 | 6/1962 | Japan. |
| 60-239438 | 11/1985 | Japan. |
| 61-501630 | 8/1986 | Japan. |
| 3-236337 | 10/1991 | Japan. |
| 4-46133 | 2/1992 | Japan. |

*Primary Examiner*—Arthur C. Prescott
*Attorney, Agent, or Firm*—Pennie & Edmonds

[57] ABSTRACT

A process for preparing adipic acid from cyclohexene oxide comprising the following steps (a) and (b):

(a) hydrating cyclohexene oxide to obtain 1,2-dihydroxycyclohexane and an oligomers represented by formula (I):

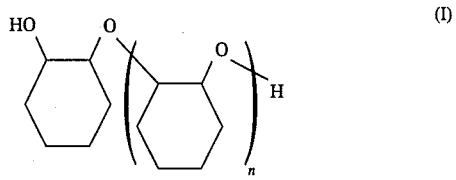

wherein n represents a number of from 1 to 5 in number average, and (b) oxidizing the 1,2-dihydroxycyclohexane and the oligomers represented by formula (I) in a nitric acid aqueous solution.

8 Claims, No Drawings

PROCESS FOR PREPARING ADIPIC ACID

This application is a 371 of PCT JP/93/00457, Apr. 9, 1993.

FIELD OF THE INVENTION

This invention relates to a process for preparing adipic acid from cyclohexene oxide.

BACKGROUND OF THE INVENTION

Dutch Patent Application No. 6601148 discloses a process for preparing adipic acid by oxidizing 1,2-dioxycyclohexane in a nitric acid aqueous solution containing a water-soluble vanadium salt. It discloses that the advantage of the process, over the currently more common process of oxidizing cyclohexanol and/or cyclohexanone with nitric acid, is that the proportion of nitric acid consumed in the form of nitrogen and nitrous oxide is reduced. However, in Example 1 in which cyclohexene oxide is used as a starting material, and nitric acid having a concentration of 70% is used as the oxidizing agent, the yield of adipic acid attained is 92%, and 0.12 mol of nitric acid is consumed in the form of nitrous oxide and nitrogen per mol of the organic starting material. In Example 4 in which 1,2-dihydroxycyclohexane is used as a starting material, and nitric acid having a concentration of 70% is used as the oxidizing agent, the yield of adipic acid is 94%, and 0.16 mol of nitric acid is consumed in the form of nitrous oxide and nitrogen per mol of the organic starting material. Therefore, while catalysis by water-soluble vanadium salts gives some improvement, the process of the Dutch application is still unsatisfactory.

while 1,2-dihydroxycyclohexane can be obtained through various processes, hydration of cyclohexene oxide derived from cyclohexene is one of the industrially more economical processes. A method of hydration of an epoxy compound is described, e.g., in *Morison Boyd Yuki Kagaku Dai-4-han* (Morison Boyd Organic Chemistry 4th edition), translated by Nakanishi et al., pp. 720–728, Tokyo Kagaku Dojin. Applicants have found that the hydration of cyclohexene oxide is accompanied by the formation of by-products consisting mainly of oligomers of cyclohexene oxide represented by formula (I):

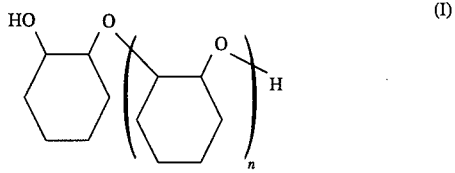

wherein n represents a number of from 1 to 5 in number average. Applicants have observed that water for hydration must be used in large excess over a theoretical amount in order to minimize the by-production of oligomers (I).

SUMMARY OF THE INVENTION

A first object of the present invention is to eliminate the above-mentioned disadvantages associated with Dutch Patent Application No. 6601148 and to establish an industrially valuable process for preparing adipic acid in an increased yield while suppressing formation of nitrous oxide and nitrogen.

The aforesaid Dutch patent application and other existing descriptions of the preparation of adipic acid from cyclohexanol and/or cyclohexanone by oxidation with nitric acid make no specific mention of how to deal with the oligomers (I). Hence, where a conventional technique is to be followed, it seems that there is no alternative but to conduct hydration of cyclohexene oxide by using a large excess of water and then to remove the excess water by energy-intensive drying or by separating the by-product oligomers (I) by distillation or a similar means. Either removal procedure would make the steps involved complicated and require a large quantity of extra energy, resulting in disadvantages in carrying out the process on an industrial scale. Accordingly, a second object of the present invention is to provide a process in which the above problem can be solved economically.

The present invention relates to a process for preparing adipic acid from cyclohexene oxide comprising the following steps (a) and (b):

(a) hydrating cyclohexene oxide to obtain 1,2-dihydroxycyclohexane and an oligomers represented by formula (I), and (b) oxidizing the 1,2-dihydroxycyclohexane and the oligomers represented by formula (I) in a nitric acid aqueous solution.

The present invention also relates to a process for preparing adipic acid from cyclohexene oxide comprising the following steps (a) and (b):

(a) hydrating cyclohexene oxide to obtain 1,2-dihydroxycyclohexane and an oligomers represented by formula (I), and (b) oxidizing the 1,2-dihydroxycyclohexane and the oligomers represented by formula (I) in a nitric acid aqueous solution, the ratio of the oligomers represented by formula (I) and the 1,2-dihydroxycyclohexane being from 60/40 to 1/99 by weight.

DETAILED DESCRIPTION OF THE INVENTION

Firstly, the inventors have found that oxidation of 1,2-dihydroxycyclohexane in a nitric acid aqueous solution having dissolved therein a catalyst comprising vanadium and at least one of metals of Groups IB, IIB, III, IV, V, VIB, VIIB, and VIII furnishes adipic acid in a high yield while surprisingly suppressing the formation of nitrous oxide and nitrogen to a substantially negligible level.

The form of vanadium is not particularly limited. Examples thereof include ammonium metavanadate, vanadium chloride, vanadyl oxalate, and vanadyl acetylacetonate.

Examples of the metals that can be used in the present invention in combination with vanadium include the Group IB metals, e.g., Cu and Ag; the Group IIB metals, e.g., Zn and Cd; the Group III metals, e.g., Al, Ga, In, and Sc; the Group IV metals, e.g., Sn, Pb, Ti, and Zr; the Group V metals, e.g., Sb, Pb, Nb, and Ta; the Group VIB metals, e.g., Cr and Mo; the Group VIIB metals, e.g., Mn; and the Group VIII metals, e.g., Fe and Co. The form of these metals may be any of those that are soluble in nitric acid, such as simple metals, inorganic salts, organic acid salts, and complexes. Specific examples thereof include nitrates, chlorides, sulfates, acetates, and acetylacetonates.

The catalyst may be used over a relatively wide range. The catalyst may range from 0.01% by weight, in terms of the total amount of metals, based on the nitric acid aqueous solution used in the reaction, up to the saturation solubility, but is generally not more than 5% by weight.

The amount of vanadium is generally from 0.01 to 5.0% by weight, and preferably from 0.01 to 2.0% by weight, in terms of the amount of metallic vanadium, based on the nitric acid aqueous solution. The amount of the metals that can be used in combination with vanadium is generally from 0.01 to 5.0% by weight, and preferably from 0.01 to 2.0% by weight, in terms of the total amount of metals, based on the nitric acid aqueous solution.

Secondly, applicants have also studied hydration of cyclohexene oxide. Use of a catalyst in hydration of cyclohexene oxide is conventionally known. Examples of known catalysts include general acidic or basic catalysts (e.g., in U.S. Pat. No. 2,576,890 and German Patent 1793247), inorganic solid acids, such as zeolite and montmorillonite (e.g., in U.S. Pat. No. 4,011,278 and JP-A-4-41449, the term "JP-A" as used herein means an "unexamined published Japanese patent application"), and ion-exchange resins (e.g., in B. C. Ranu and R. Chakraborty, Synthetic communications, Vol. 20, No. 12, pp. 1751–1767 (1990)). Applicants have found that hydration of cyclohexene oxide is unavoidably accompanied by by-production of the oligomers of formula (I) even in the presence of these catalysts. It was also found that water of hydration must be used in large excess over the theoretical amount in order to minimize the by-production of the oligomers. As none of the conventional techniques of oxidation with nitric acid refers to handling of the oligomers of formula (I), applicants made a further study of this problem.

It has been surprisingly found that the oligomers of formula (I) are easily oxidized with nitric acid to produce adipic acid in high yield with the proportion of nitric acid lost as nitrogen or nitrous oxide being far less than in the conventional nitric acid oxidation of cyclohexanol or cyclohexanone. In formula (I), n is preferably in the range of from 1 to 5 in number average. If n is more than this range, the yield of adipic acid is reduced.

Applicants have found a further surprising fact, namely, that oxidation of a mixture of the oligomers of formula (I) and 1,2-dihydroxycyclohexane in a nitric acid aqueous solution results in a reduction of the consumption of nitric acid and an increase of the yield of adipic acid. According to the investigations by the applicants, the amount of nitrous oxide produced by oxidizing of the mixture of the oligomers of formula (I) and 1,2-dihydroxycyclohexane in a nitric acid aqueous solution is less than the summation average of the cases where each of them is separately oxidized, and the yield of adipic acid is improved. This effect, while occurring at any arbitrary mixing ratio, is especially noticeable at a weight ratio of the oligomers of formula (I) to 1,2-dihydroxycyclohexane of from 60/40 to 1/99. Based on this fact, the inventors have established the technique by which even if the oligomers of formula (I) are produced in the step (a) hydration of cyclohexene oxide, they are successively oxidized with nitric acid together with 1,2-dihydroxycyclohexane, etc. and converted to adipic acid at a high yield, with the proportion of consumed nitric acid being remarkably reduced. The 1,2-dihydroxycyclohexane to be mixed here may be the cis-form, the trans-form, or mixtures thereof. Where both 1,2-dihydroxycyclohexane and cyclohexene oxide are used, the mixing ratio thereof is arbitrary.

Where the oligomers of formula (I) or a mixture of the oligomers of formula (I) and 1,2-dihydroxycyclohexane is oxidized with nitric acid, it is preferable to use vanadium either alone or in combination with at least one of the metals of Groups IB, IIB, III, IV, V, VIB, VIIB, and VIII as a catalyst. The form of the metals may be any of those which are soluble in nitric acid, such as simple metals, inorganic salts, organic acid salts, and complexes. The amount of the catalyst that can be used may vary over a relatively wide range. The catalyst may range from 0.01% by weight, in terms of the total amount of metals, based on the nitric acid aqueous solution used in the reaction, up to the saturation solubility, but is generally not more than 5% by weight.

Although the mode of oxidation with reduced generation of nitrogen or nitrous oxide has the great merit of decreased consumption of nitric acid as stated above, it is necessary to take into consideration that slight disadvantages may develop in industrial production. That is, the proportion of nitric acid consumed in the form of $N_2O$ and $N_2$ is greatly reduced but, instead, the amount of gases driven out of the reaction system, such as NO and $NO_2$ (hereinafter inclusively referred to NOX), may greatly increase, and a large-sized apparatus would be needed for recovery of the gases. Applicants have found that release of NOX out of the reaction system during oxidation of 1,2-dihydroxycyclohexane and/or the oligomers of formula (I) with nitric acid to obtain adipic acid can be inhibited by introducing oxygen or an oxygen-containing gas into the reaction system. In this case, the yield of adipic acid was found to be further improved.

In step (a) according to the process of the present invention, water should be used in an amount not less than the theoretical amount, and generally is used in an amount in the range of from 0.25 to 10 times the weight of cyclohexene oxide. If the amount of water is less than this range, the reaction rate is considerably lowered. If it is more than this range, a large quantity of energy would be required for separation of excess water.

It is also possible to use a catalyst accelerating the hydration reaction of cyclohexene oxide. Examples of suitable catalysts include general acid or basic catalysts (e.g., in U.S. Pat. No. 2,576,890 and German Patent 1793247) and, in addition, those capable of hydrating an epoxy compound, such as inorganic solid acids, e.g., zeolite and montmorillonite (e.g., in U.S. Pat. No. 4,011,278 and JP-A-4-41449), and ion-exchange resins (e.g., in B. C. Ranu and R. Chakraborty, *Synthetic communications*, Vol. 20, No. 12, pp. 1751–1767 (1990)). The amount of the catalyst to be used is usually not less than 0.01 mol % based on cyclohexene oxide as an acid or a base, while varying depending on the kind of the catalyst used and the conditions.

The temperature of the hydration reaction is not particularly critical and is usually in the range of from room temperature to 200° C.

While it is not essential to completely hydrate cyclohexene oxide, the conversion of cyclohexene oxide is generally 50% or more, and preferably 70% or more.

In cases where the conversion of cyclohexene oxide in step (a) is not 100%, the reaction mixture as obtained is a mixture containing cyclohexene oxide as well as 1,2-dihydroxycyclohexane and the oligomers of formula (I). It was ascertained that oxidation of a mixture of the oligomers of formula (I), 1,2-dihydroxycyclohexane, and cyclohexene oxide in a nitric acid aqueous solution produces the same effects as observed in oxidation of a mixture of the oligomers of formula (I) and 1,2-dihydroxycyclohexane in a nitric acid aqueous solution. In other words, the amount of nitrous oxide produced in oxidation of the mixture of the oligomers of formula (I), 1,2-dihydroxycyclohexane, and cyclohexene oxide mixture in a nitric acid aqueous solution is less than the summation average in the cases where each of them is separately oxidized, and the yield of adipic acid is improved. This effect, while occurring at any arbitrary mixing ratio, is especially noticeable at a weight ratio of the oligomers of formula (I) to 1,2-dihydroxycyclohexane of from 60/40 to 1/99, and particularly from 50/50 to 1/99.

If the reaction temperature in step (b) is too low, the reaction rate is reduced, and if it is too high, side reactions increase. Accordingly, the reaction temperature will generally range from 20° to 120° C., and preferably from 30° to 90° C.

The reaction of step (b) is carried out by using nitric acid at concentrations ranging from 10 to 80% by weight, and preferably from 30 to 70% by weight.

The molar ratio of cyclo-rings to nitric acid in step (b) is generally not less than 2, and preferably not less than 3.

The reaction mixture as obtained from step (a) may be subjected to step (b) either as such or after being concentrated by, for example, evaporating excess water. It is also possible to separate part or all of the 1,2-dihydroxycyclohexane and/or unreacted cyclohexene oxide obtained in step (a) by, for example, distillation. Each of the residues containing the thus separated 1,2-dihydroxycyclohexane and/or cyclohexene oxide or the oligomers of formula (I) may be individually used in step (b).

Even where by-products other than oligomers (I) in step (a), for example, nitrated 1,2-dihydroxycyclohexane, a by-product of hydration with nitric acid, are produced, they may be subjected to step (b) together with 1,2-dihydroxycyclohexane and/or cyclohexene oxide and/or the oligomers of formula (I) as long as the effects of the present invention are not seriously impaired.

In carrying out the reaction, a solvent inert to the reaction, such as water, may be added to the starting mixture of the oligomers of formula (I) and/or 1,2-dihydroxycyclohexane and/or cyclohexene oxide.

In the process of the present invention, additional use of the oligomers of formula (I) or 1,2-dihydroxycyclohexane that have been prepared by any process other than hydration of cyclohexene oxide is also contemplated. Examples of other processes for preparing the oligomers of formula (I) include, for example, dehydrating condensation of 1,2-dihydroxycyclohexane, ring-opening polymerization of cyclohexene oxide, addition reaction of 1,2-dihydroxycyclohexane and cyclohexene oxide, and substitution reaction of di(2-chlorocyclohexyl)ether, etc. with a hydroxyl group. Examples of other processes for preparing 1,2-dihydroxycyclohexane include hydrogenation of catechol.

The reaction of the present invention may be carried out either in a batch mode or in a continuous system. In particular, the reaction system conventionally employed for oxidation of cyclohexanol or cyclohexanone in a nitric acid aqueous solution may suitably be applied to step (b).

The present invention will now be illustrated in greater detail by way of Examples, but the present invention should not be construed as being limited thereto.

The adipic acid yields in Examples and Comparative Examples were expressed in terms of molar yield based on the cyclo-rings contained in the starting mixture of the oligomers of formula (I), 1,2-dihydroxycyclohexane, cyclohexene oxide, etc.

EXAMPLE 1

Hydration of Cyclohexene Oxide:
A reactor was charged with 100 g of water and 10 g of a cation exchange resin ("Daiaion SK1BH" produced by Mitsubishi Chemical Corporation). Then 100 g of cyclohexene oxide was added thereto dropwise over about 30 minutes while stirring at 80° C. The stirring was continued for an additional period of 30 minutes. The cation exchange resin was separated from the reaction mixture by filtration and washed with 30 g of water. The washing and the filtrate were combined and analyzed to find that the conversion of cyclohexene oxide was 99.7% and the yields of 1,2-dihydroxycyclohexane and a dimer of formula (I) wherein n=1 were 90.2% and 9.5%, respectively.

Oxidation in Nitric Acid Aqueous Solution:
The reaction mixture was concentrated under reduced pressure to a water content of 20% by weight. 30.0 g of the concentrate were added to 250 g of 60% nitric acid containing 0.230% by weight of ammonium metavanadate kept at 80° C. over 30 minutes. The reaction was continued at 80° C. for 30 minutes, and the resulting reaction mixture and released gaseous components were analyzed. Adipic acid was obtained in a yield of 95.7%. The amount of nitric acid converted to nitrogen and nitrous oxide was 0.039 kg per kg of the produced adipic acid. The amount of the released NOX was found to correspond to 3.3 times the mole number of the cyclo-rings in the starting materials.

COMPARATIVE EXAMPLE 1

Hydration of Cyclohexene Oxide:
A reactor was charged with 100 g of water and 10 g of a cation exchange resin ("Daiaion SK1BH" produced by Mitsubishi Chemical Corporation). Then 100 g of cyclohexene oxide was added thereto dropwise over about 30 minutes while stirring at 80° C. The stirring was continued for an additional period of 30 minutes. The cation exchange resin was separated from the reaction mixture by filtration and washed with 30 g of water. The washing and the filtrate were combined and analyzed to find that the conversion of cyclohexene oxide was 99.7% and the yields of 1,2-dihydroxycyclohexene and a dimer of formula (I) wherein n=1 were 90.2% and 9.5%, respectively.

Oxidation in Nitric Acid Aqueous Solution:
The reaction mixture was distilled under reduced pressure to obtain 1,2-dihydroxycyclohexane having a purity of 99.7% or higher. 25.0 g of the resulting 1,2-dihydroxycyclohexane were added to 250 g of 60% nitric acid containing only 0.230% by weight of ammonium metavanadate and no additional metal species kept at 80° C. over 30 minutes. The reaction was continued at 80° C. for an additional period of 30 minutes, and the resulting reaction mixture and released gaseous components were analyzed. Adipic acid was obtained in a yield of 95.8%. The amount of nitric acid converted to nitrogen and nitrous oxide was 0.080 kg per kg of the produced adipic acid. The amount of the released NOX was found to correspond to 3.0 times the mole number of the cyclo-rings in the starting materials.

It is understood from the results of Example 1 and Comparative Example 1 that Example 1, where a mixture of 1,2-dihydroxycyclohexane and a dimer of formula (I) is oxidized in a nitric acid aqueous solution, results in lower consumption of nitric acid, in comparison to Comparative Example 1, where only 1,2-dihydroxycyclohexane is oxidize.

COMPARATIVE EXAMPLE 2

Oxidation in a nitric acid aqueous solution was conducted by adding 24 g of cyclohexene oxide to 250 g of 60% nitric acid containing only 0,230% by weight of ammonium metavanadate and no additional metal species over 30 minutes. The reaction was continued at 80° C. for 30 minutes, and the resulting reaction mixture and released gaseous components were analyzed. Adipic acid was obtained in a yield of 83.7%. The amount of nitric acid converted to nitrogen and nitrous oxide was 0.172 kg per kg of the produced adipic acid. The amount of the released NOX was found to correspond to 2.6 times the mole number of the cyclo-rings in the starting materials.

It is understood from the results of Example 1 and Comparative Example 2 that Example 1, where a mixture of 1,2-dihydroxycyclohexane and a dimer of formula (I) is oxidized in a nitric acid aqueous solution, is superior in yield of adipic acid, consumption of nitric acid, and NOX formation, in comparison to Comparative Example 2, where cyclohexene oxide is directly oxidized.

REFERENCE EXAMPLE 1

A conventional process for preparing adipic acid by oxidizing cyclohexanol, which has been widely used in this field of art, was conducted. Oxidation in a nitric acid aqueous solution was conducted by adding 24 g of cyclohexanol to 250 g of 60% nitric acid containing only 0.230% by weight of ammonium metavanadate and no additional metal species over 30 minutes. The reaction was continued at 80° C. for 30 minutes, and the resulting reaction mixture and released gaseous components were analyzed. Adipic acid was obtained in a yield of 88%. The amount of nitric acid converted to nitrogen and nitrous oxide was 0.724 kg per kg of the produced adipic acid. The amount of the released NOX was found to correspond to 0.7 times the mole number of the cyclo-rings in the starting materials.

EXAMPLE 2

Hydration of Cyclohexene Oxide:

A reactor was charged with 650 g of water and 25 g of Y-type zeolite. Then 1,000 g of cyclohexene oxide was added thereto dropwise over about 30 minutes while stirring at 80° C. The stirring was continued for an additional period of 30 minutes. As a result of the analyses of the reaction mixture, the conversion of cyclohexene oxide was 70.0% and the yields of 1,2-dihydroxycyclohexane and a dimer of formula (I) wherein n=1 were 60.0% and 8.7%, respectively.

Oxidation in Nitric Acid Aqueous Solution:

Zeolite was removed from the reaction mixture by filtration, and the filtrate was distilled under reduced pressure to remove water, cyclohexene oxide, and 1,2-dihydroxycyclohexane to recover a mixture comprising 85% by weight of a dimer of formula (I) wherein n=1 and 14% by weight of a trimer of formula (I) wherein n=2. 25.0 g of the mixture were added to 250 g of 60% nitric acid containing 0.230% by weight of ammonium metavanadate kept at 80° C. over 30 minutes. The reaction was continued at 80° C. for an additional period of 30 minutes, and the resulting reaction mixture and released gaseous components were analyzed. Adipic acid was obtained in a yield of 86.0%. The amount of nitric acid converted to nitrogen and nitrous oxide was 0,110 kg per kg of the produced adipic acid. The amount of the released NOX was found to correspond to 2.9 times the mole number of the cyclo-rings in the starting materials.

EXAMPLES 3 TO 10

Oxidation in a nitric acid aqueous solution was conducted in the same manner as in Example 2, except that the catalyst of Example 2 was replaced by each of the catalysts shown in Table 1 below. The reaction results are shown in Table 1.

TABLE

| | Example 3 | Example 4 | Example 5 | Example 6 | Example 7 | Example 8 | Example 9 | Example 10 |
|---|---|---|---|---|---|---|---|---|
| Catalyst Composition (wt % in 60% HNO$_3$) | NH$_4$VO$_3$ (0.23) Cu(NO$_3$)$_2$ (2.95) | NH$_4$VO$_3$ (0.23) Zn(NO$_3$)$_3$ (1.00) | NH$_4$VO$_3$ (0.23) Al(NO$_3$)$_4$ (1.00) | NH$_4$VO$_3$ (0.23) Zr(NO$_3$)$_3$ (1.00) | NH$_4$VO$_3$ (0.23) Bi(NO$_3$)$_3$ (1.00) | NH$_4$VO$_3$ (0.23) Cr(NO$_3$)$_3$ (1.00) | NH$_4$VO$_3$ (0.23) Mn(NO$_3$)$_2$ (1.00) | NH$_4$VO$_3$ (0.23) Co(NO$_3$)$_3$ (1.00) |
| Adipic Acid Yield*[1] (%) | 89.0 | 87.1 | 87.0 | 87.2 | 87.1 | 88.0 | 87.9 | 88.1 |
| Nitric Acid Consumption*[2] | 0.088 | 0.091 | 0.090 | 0.090 | 0.089 | 0.089 | 0.091 | 0.090 |
| Amount of NOX Generated*[3] | 3.5 | 3.5 | 3.6 | 3.5 | 3.6 | 3.5 | 3.5 | 3.6 |

Note:
*[1] Molar yield (%) based on cyclo-rings in the starting materials.
*[2] Kilograms per kg of produced adipic acid.
*[3] Number of times based on mole number of cyclo-rings in the starting materials.

EXAMPLE 11

Hydration of Cyclohexene Oxide:

A reactor was charged with 100 g of water and 10 g of a cation exchange resin ("Daiaion SK1BH" produced by Mitsubishi Chemical Corporation). Then 100 g of cyclohexene oxide was added thereto dropwise over about 30 minutes while stirring at 80° C. The stirring was continued for an additional period of 30 minutes. The cation exchange resin was separated from the reaction mixture by filtration and washed with 30 g of water. The washing and the filtrate were combined and analyzed to find that the conversion of cyclohexene oxide was 99.7% and the yields of 1,2-dihydroxycyclohexane and a dimer of formula (I) wherein n=1 were 90.2% and 9.5%, respectively.

Oxidation in Nitric Acid Aqueous Solution:

The reaction mixture was distilled under reduced pressure to remove water, 1,2-dihydroxycyclohexane, etc. to thereby obtain a mixture comprising 70.0% by weight of 1,2-dihydroxycyclohexane and 30.0% by weight of an oligomers of formula (I). 25.0 g of the resulting mixture were added to 250 g of 60% nitric acid containing 0.230% by weight of ammonium metavanadate kept at 80° C. over 30 minutes. The reaction was continued at 80° C. for 30 minutes, and the resulting reaction mixture and released gaseous components were analyzed. Adipic acid was obtained in a yield of 94.8%. The amount of nitric acid converted to nitrogen and nitrous oxide was 0,051 kg per kg of the produced adipic acid. The amount of the released NOX was found to correspond to 3.2 times the mole number of the cyclo-rings in the starting materials.

EXAMPLES 12 TO 15

A reaction was carried out in the same manner as in Example 11, except that the distillation for removal of water, 1,2-dihydroxycyclohexane, etc. was controlled so as to obtain a residue containing 1,2-dihydroxycyclohexane and oligomers (I) at a ratio shown in Table 2 below. The reaction results obtained are shown in Table 2.

TABLE 2

|  | Example 12 | Example 13 | Example 14 | Example 15 |
|---|---|---|---|---|
| 1,2-Dihydroxycyclo-hexane/Oligomers (I) Weight Ratio | 50/50 | 30/70 | 10/90 | 1/99 |
| Adipic Acid Yield*[1] (%) | 93.2 | 89.6 | 87.2 | 86.0 |
| Nitric Acid Consumption*[2] | 0.065 | 0.082 | 0.101 | 0.110 |
| Amount of NOX Generated*[3] | 3.1 | 3.0 | 2.9 | 2.9 |

Note:
*[1])Molar yield based on cyclo-rings in the starting materials.
*[2])Kilograms per kg of produced adipic acid.
*[3])Number of times based on mole number of cyclo-rings in the starting materials.

EXAMPLES 16 TO 23

Oxidation in a nitric acid aqueous solution was carried out in the same manner as in Example 11, except that the catalyst of Example 11 was replaced by each of the catalysts shown in Table 3 below. The results obtained are shown in Table 3.

TABLE 3

|  | Example 16 | Example 17 | Example 18 | Example 19 | Example 20 | Example 21 | Example 22 | Example 23 |
|---|---|---|---|---|---|---|---|---|
| Catalyst Composition (wt % in 60% HNO₃) | $NH_4VO_3$ (0.46) $Cu(NO_3)_2$ (2.95) | $NH_4VO_3$ (0.46) $Zn(NO_3)_3$ (1.00) | $NH_4VO_3$ (0.46) $Al(NO_3)_4$ (1.00) | $NH_4VO_3$ (0.46) $Zr(NO_3)_3$ (1.00) | $NH_4VO_3$ (0.46) $Bi(NO_3)_3$ (1.00) | $NH_4VO_3$ (0.46) $Cr(NO_3)_3$ (1.00) | $NH_4VO_3$ (0.46) $Mn(NO_3)_2$ (1.00) | $NH_4VO_3$ (0.46) $Co(NO_3)_3$ (1.00) |
| Adipic Acid Yield*[1] (%) | 95.7 | 95.1 | 95.0 | 95.2 | 95.2 | 95.4 | 95.1 | 95.4 |
| Nitric Acid Consumption*[2] | 0.049 | 0.049 | 0.050 | 0.050 | 0.050 | 0.049 | 0.049 | 0.048 |
| Amount of NOX Generated*[3] | 3.4 | 3.4 | 3.6 | 3.5 | 3.6 | 3.6 | 3.5 | 3.5 |

Note:
*[1])Molar yield (%) based on cyclo-rings in the starting materials.
*[2])Kilograms per kg of produced adipic acid.
*[3])Number of times based on mole number of cyclo-rinqs in the starting materials.

EXAMPLE 24

Oxidation in a nitric acid aqueous solution was carried out in the same manner as in Example 11, except that air was bubbled through a capillary into the nitric acid aqueous solution at a rate of 70 Nl/hr. Adipic acid was obtained in a yield of 95.2%. The amount of nitric acid converted to nitrogen and nitrous oxide was 0,052 kg per kg of the produced adipic acid. The amount of the released NOX was found to correspond to 1.7 times the mole number of the cyclo-rings in the starting materials.

EXAMPLE 25

Oxidation in a nitric acid aqueous solution was carried out in the same manner as in Example 16, except that air was bubbled through a capillary into the nitric acid aqueous solution at a rate of 70 Nl/hr. Adipic acid was obtained in a yield of 95.9%. The amount of nitric acid converted to nitrogen and nitrous oxide was 0,052 kg per kg of the produced adipic acid. The amount of the released NOX was found to correspond to 1.8 times the mole number of the cyclo-rings in the starting materials.

EXAMPLES 26 TO 29 AND REFERENCE EXAMPLE 2

Hydration of Cyclohexene Oxide:

A reactor was charged with 650 g of water and 25 g of Y-type zeolite. Then 1,000 g of cyclohexene oxide was added thereto dropwise over about 30 minutes while stirring at 80° C. The stirring was continued for an additional period of 30 minutes. As a result of the analyses of the reaction mixture, the conversion of cyclohexene oxide was 70.0% and the yields of 1,2-dihydroxycyclohexane and a dimer of formula (I) wherein n=1 were 60.0% and 9.0%, respectively.

Oxidation in Nitric Acid Aqueous Solution:

Zeolite was removed from the reaction mixture by filtration, and the filtrate was distilled under reduced pressure to remove water, cyclohexene oxide, and 1,2-dihydroxycyclohexane to thereby recover a mixture comprising 85% by weight of a dimer of formula (I) wherein n=1, 14% by weight of a trimer of formula (I) wherein n=2, and 1% by weight of 1,2-dihydroxycyclohexane. The resulting mixture was mixed with the above separated cyclohexene oxide and 1,2-dihydroxycyclohexane to prepare a mixture having the composition shown in Table 4 below.

Oxidation in Nitric Acid Solution:

25.0 g of the thus prepared mixture were added to 250 g of 60% nitric acid containing 0,230% by weight of ammonium metavanadate kept at 80° C. over 30 minutes. The reaction was continued at 80° C. for 30 minutes, and the resulting reaction mixture and released gaseous components were analyzed. The results obtained are shown in Table 4.

TABLE 4

|  | Example 26 | Example 27 | Example 28 | Example 29 | Reference Example 2 |
|---|---|---|---|---|---|
| Oligomers (I)/1,2-Dihydroxycyclohexane/Cyclohexene Oxide Weight Ratio | 10/60/30 | 30/46.7/23.3 | 50/33.3/16.7 | 70/20/10 | 0/66.7/33.3 |
| Adipic Acid Yield*[1] (%) | 90.8 | 90.4 | 89.3 | 87.9 | 91.0 |
| Nitric Acid Consumption*[2] | 0.097 | 0.099 | 0.102 | 0.105 | 0.95 |
| Amount of NOX Generated*[3] | 3.0 | 3.0 | 2.9 | 2.9 | 3.0 |

Note:
*[1]Molar yield (%) based on cyclo-rings in the starting materials.
*[2]Kilograms per kg of produced adipic acid.
*[3]Number of times based on mole number of cyclo-rings in the starting materials.

EXAMPLES 30 TO 37

Oxidation in a nitric acid aqueous solution was carried out in the same manner as in Example 26, except that the catalyst of Example 26 was replaced by each of the catalysts shown in Table 5 below. The reaction results are shown in Table 5.

EXAMPLE 38

Oxidation in a nitric acid aqueous solution was carried out in the same manner as in Example 26, except that air was bubbled through a capillary into the nitric acid aqueous solution at a rate of 70 Nl/hr. Adipic acid was obtained in a yield of 91.4%. The amount of nitric acid converted to nitrogen and nitrous oxide was 0.096 kg per kg of the produced adipic acid. The amount of the released NOX was found to correspond to 1.8 times the mole number of the cyclo-rings in the starting materials.

EXAMPLE 39

Oxidation in a nitric acid aqueous solution was carried out in the same manner as in Example 1, except that the reaction temperature was changed to 60° C. Adipic acid was obtained in a yield of 96.6%. The amount of nitric acid converted to nitrogen and nitrous oxide was 0.038 kg per kg of the produced adipic acid. The amount of the released NOX was found to correspond to 3.3 times the mole number of the cyclo-rings in the starting materials.

TABLE 5

|  | Example 30 | Example 31 | Example 32 | Example 33 | Example 34 | Example 35 | Example 36 | Example 37 |
|---|---|---|---|---|---|---|---|---|
| Catalyst Composition (wt % in 60% HNO$_3$) | NH$_4$VO$_3$ (0.46) Cu(NO$_3$)$_2$ (2.95) | NH$_4$VO$_3$ (0.46) Zn(NO$_3$)$_3$ (1.00) | NH$_4$VO$_3$ (0.46) Al(NO$_3$)$_4$ (1.00) | NH$_4$VO$_3$ (0.46) Zr(NO$_3$)$_3$ (1.00) | NH$_4$VO$_3$ (0.46) Bi(NO$_3$)$_3$ (1.00) | NH$_4$VO$_3$ (0.46) Cr(NO$_3$)$_3$ (1.00) | NH$_4$VO$_3$ (0.46) Mn(NO$_3$)$_2$ (1.00) | NH$_4$VO$_3$ (0.46) Co(NO$_3$)$_3$ (1.00) |
| Adipic Acid Yield*[1] (%) | 92.2 | 91.6 | 91.5 | 91.6 | 91.4 | 91.8 | 91.7 | 91.5 |
| Nitric Acid Consumption*[2] | 0.094 | 0.093 | 0.096 | 0.094 | 0.094 | 0.094 | 0.093 | 0.093 |
| Amount of NOX Generated*[3] | 3.0 | 3.0 | 3.0 | 3.1 | 3.0 | 3.1 | 3.0 | 3.0 |

Note:
*[1]Molar yield (%) based on cyclo-rings in the starting materials.
*[2]Kilograms per kg of produced adipic acid.
*[3]Number of times based on mole number of cyclo-rings in the starting materials.

The process of the present invention makes it possible to obtain adipic acid from cyclohexene oxide in a high yield while significantly minimizing consumption of nitric acid, thereby achieving preparation of adipic acid at low cost.

While the invention has been described in detail and with reference to specific examples thereof, it will be apparent to one skilled in the art that various changes and modifications can be made therein without departing from the spirit and scope thereof.

We claim:

1. A process for preparing adipic acid from cyclohexene oxide comprising the following steps (a) and (b):

(a) hydrating cyclohexene oxide to obtain 1,2-dihydroxycyclohexane and an oligomers represented by formula (I):

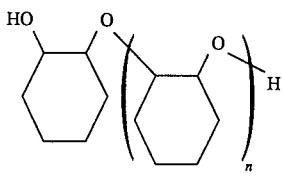

wherein n represents a number of from 1 to 5 in number average, and (b) oxidizing the 1,2-dihydroxycyclohexane and the oligomers represented by formula (I) in a nitric acid aqueous solution.

2. A process for preparing adipic acid from cyclohexene oxide comprising the following steps (a) and (b):

(a) hydrating cyclohexene oxide to obtain 1,2-dihydroxycyclohexane and an oligomers represented by formula (I):

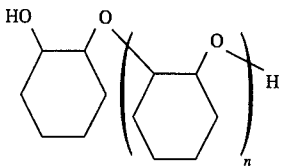

wherein n represents a number of from 1 to 5 in number average, and (b) oxidizing the 1,2-dihydroxycyclohexane and the oligomers represented by formula (I) in a nitric acid aqueous solution, the ratio of the oligomers represented by formula (I) and the 1,2-dihydroxycyclohexane being from 60/40 to 1/99 by weight.

3. A process as in claim 1, wherein the oxidation of the 1,2-dihydroxycyclohexane and the oligomers represented by formula (I) in a nitric acid aqueous solution is carried out in the presence of a catalyst comprising dissolved vanadium or a catalyst comprising dissolved vanadium and at least one dissolved metal selected from the metals of Groups IB, IIB, III, IV, V, VIB, VIIB, and VIII.

4. A process as in claim 2, wherein the oxidation of the 1,2-dihydroxycyclohexane and the oligomers represented by formula (I) in a nitric acid aqueous solution is carried out in the presence of a catalyst comprising dissolved vanadium or a catalyst comprising dissolved vanadium and at least one dissolved metal selected from the metals of Groups IB, IIB, III, IV, V, VIB, VIIB, and VIII.

5. A process as in claim 1, wherein the oxidation of the 1,2-dihydroxycyclohexane and the oligomers represented by formula (I) in a nitric acid aqueous solution is carried out while bubbling oxygen or an oxygen-containing gas into the oxidation reaction system.

6. A process as in claim 2, wherein the oxidation of the 1,2-dihydroxycyclohexane and the oligomers represented by formula (I) in a nitric acid aqueous solution is carried out while bubbling oxygen or an oxygen-containing gas into the oxidation reaction system.

7. A process as in claim 3, wherein the oxidation of the 1,2-dihydroxycyclohexane and the oligomers represented by formula (I) in a nitric acid aqueous solution is carried out while bubbling oxygen or an oxygen-containing gas into the oxidation reaction system.

8. A process as in claim 4, wherein the oxidation of the 1,2-dihydroxycyclohexane and the oligomers represented by formula (I) in a nitric acid aqueous solution is carried out while bubbling oxygen or an oxygen-containing gas into the oxidation reaction system.

* * * * *